United States Patent [19]

Kruse et al.

[11] Patent Number: 5,387,721
[45] Date of Patent: Feb. 7, 1995

[54] METHYL TERTIARY BUTYL ETHER PROCESS

[75] Inventors: Charles J. Kruse, Cypress; Kyle L. Preston, Port Arthur; Brian L. Benac, San Marcos, all of Tex.

[73] Assignee: Texaco Inc., White Plains, N.Y.

[21] Appl. No.: 170,849

[22] Filed: Dec. 21, 1993

[51] Int. Cl.$^6$ .................... C07C 41/09; C07L 41/06
[52] U.S. Cl. .................... 568/697; 568/698; 568/699
[58] Field of Search .................... 568/697, 698, 699

[56] References Cited

U.S. PATENT DOCUMENTS 5,243,091  9/1993  Kruse et al. .................... 568/697

Primary Examiner—Howard T. Mars
Attorney, Agent, or Firm—James L. Bailey; Kenneth R. Priem; Richard A. Morgan

[57] ABSTRACT

Methyl tertiary butyl ether (MTBE) is formed by reaction of methanol with tertiary butyl ether in two catalyst beds. A feedstock mixture comprising methanol and tertiary butyl alcohol in a molar ratio of 2 to 3 moles of methanol per mole of tertiary butyl alcohol is reacted in a first etherification reaction zone at a liquid hourly space velocity of 1 to 10 volumes of feedstock mixture per volume of catalyst per hour. A first reaction product mixture is fractionated to remove unreacted methanol, isobutylene and MTBE overhead. This isobutylene is passed to a second etherification reaction zone at a liquid hourly space velocity of 1 to 10. A second reaction product mixture is fractionated to recover additional MTBE.

4 Claims, No Drawings

5,387,721

METHYL TERTIARY BUTYL ETHER PROCESS

BACKGROUND OF THE INVENTION

1. Field Of the Invention

The invention relates to a process for the manufacture and purification of methyl tertiary butyl ether. More particularly, the invention relates to a continuous process for the reaction of tertiary butyl alcohol with methanol and purification of the methyl tertiary butyl ether containing reaction product mixture formed by the reaction.

2. Related Methods In The Field

Concern for environmental pollution and human health disorders caused by lead from exhaust gases of internal combustion engines has motivated a reformulation of automobile gasoline to remove lead containing compounds. In order to make an unleaded gasoline of the same octane number, high octane oxygenated hydrocarbon compounds have been substituted for tetraethyl lead in the automobile gasoline formula.

A number of oxygenated hydrocarbon compounds are known to have high octane numbers. In particular, methyl t-butyl ether (MTBE), ethyl t-butyl ether (ETBE), isopropyl t-butyl ether, t-amyl methyl ether (TAME) and t-butyl alcohol (tBA) are used commercially to increase the octane number of automobile gasoline. The preparation of these ethers by the catalytic addition of an alcohol to an olefin having a double bond adjacent a tertiary carbon atom has been extensively studied. Macroreticular acid resin catalysts are preferred catalysts for the process.

U.S. Pat. No. 5,243,091 to C. J. Kruse et al. teaches a method for preparing methyl tertiary butyl ether from methanol and tertiary butyl alcohol. Isobutylene is used downstream of the etherification reaction zone as an extractant in the purification of methyl tertiary butyl ether. Isobutylene is also reacted with methanol to yield additional methyl tertiary butyl ether.

SUMMARY OF THE INVENTION

Tertiary butyl alcohol is reacted with methanol to produce methyl tertiary butyl ether. The reaction is carried out in two catalytic reaction zones.

The feedstock comprises a mixture of methanol and tertiary butyl alcohol in a molar ratio of 2 to 3 moles of methanol per mole of tertiary butyl alcohol.

All of the feedstock is passed to the first reaction zone at a liquid hourly space velocity of 1 to 10 volumes of feedstock per volume of catalyst per hour. The first reaction product mixture is fractionated to yield a first lighter distillate fraction comprising isobutylene, methanol and methyl tertiary butyl ether and a second heavier distillate fraction comprising methanol, tertiary butyl alcohol and water.

The first lighter distillate fraction is passed to the second reaction zone at a liquid hourly space velocity of 1 to 10 volumes of feedstock per volume of catalyst per hour. The second reaction product mixture comprises isobutylene, methanol, methyl tertiary butyl ether and a small amount of tertiary butyl alcohol. This second reaction product is water washed to remove methanol an tertiary butyl alcohol. Methyl tertiary butyl ether is recovered.

The methanol and tertiary butyl alcohol are recycled to produce more methyl tertiary butyl ether.

DETAILED DESCRIPTION OF THE INVENTION

In accordance with the methyl tertiary butyl ether (MTBE) manufacture and purification method of the present invention, two separate etherification reaction zones, each containing a bed of etherification catalyst are utilized. A wide variety of etherification catalysts can be used for this purpose, such as supported acid-type catalysts. A preferred catalyst is a sulfonic acid resin etherification catalyst such as a sulfonated polystyrene resin cross-linked with divinyl benzene.

Any suitable solid resin etherification catalyst may be used for this purpose, such as a strongly acidic ion exchange resin consisting essentially of sulfonated polystyrene, such as a divinyl benzene cross-link polystyrene matrix containing from about 0.5 to about 20% of copolymerized divinyl benzene. Resins of this nature are manufactured and sold commercially under various trade names such as Dowex® 50, Dowex® M-31, Nalcite® HCR, Amberlyst® 16 and Amberlyst® 15. The use of this type of catalyst is disclosed, for example, in U.S. Pat. No. 4,144,138 to Rao.

Also, Kieselguhr impregnated with phosphoric acid as disclosed in U.S. Pat. No. 2,282,469 to Frolich, titania having phosphoric acid impregnated thereon as disclosed in U.S. Pat. No. 4,822,921 to Knifton, or a heteropolyacid such as 12-tungstophosphoric acid or 12-molybdophosphoric acid supported on titania, etc. may be used.

Zeolites or aluminosilicate zeolites as disclosed in U.S. Pat. No. 4,058,576 to Chang et al. may also be used.

The reaction conditions to be utilized when reacting methanol with tertiary butyl alcohol in the presence of a sulfonic acid resin etherification catalyst include a reaction temperature of about 35° C. to about 140° C., a pressure of about 30 psia to about 500 psia and a space velocity of about 0.5 to about 20 volumes of feed per volume of etherification catalyst per hour.

In accordance with the present invention, a distillate fraction obtained during the recovery process, identified as a first lighter distillation fraction, and which contains methanol, isobutylene, and methyl tertiary butyl ether is brought into contact with a solid resin etherification catalyst, in order to convert a significant portion of the methanol and residual isobutylene to methyl tertiary butyl ether.

Any suitable solid resin etherification catalyst may be used for this purpose. Preferred are the strongly acidic ion exchange resin consisting essentially of sulfonated polystyrene, such as a divinyl benzene cross-link polystyrene matrix containing from about 0.5% to about 20% of copolymerized divinyl benzene. Resins of this nature are manufactured and sold commercially under various trade names such as Dowex® 50, Dowex® M-31, Nalcite® HCR, Amberlyst® 16 and Amberlyst® 15. The use of catalyst of this nature is disclosed, for example, U.S. Pat. No. 4,144,138 to Rao.

The first distillation fraction will normally contain from about 5 wt % to about 15 wt % of isobutylene, from about 70 wt % to about 80 wt % of methyl tertiary butyl ether and from about 10 wt % to about 20 wt % of methanol.

The second distillation fraction will normally contain from about 40 wt % to about 60 wt % of methanol, from about 20 wt % to about 40 wt % of tertiary butyl alcohol, from about 15 wt % to about 35 wt % of water and less than 1 wt % methyl tertiary butyl ether.

The first distillation fraction is contacted with a solid resin etherification catalyst in the second etherification reaction zone under conversion conditions including, for example, a temperature of about 35° C. to about 130° C., a pressure of about 30 psia to about 500 psia and a contact time of about 1 to about 10 volumes of second distillation fraction per volume of etherification catalyst per hour. As a consequence, a second reaction product mixture is formed which will normally contain from about 1 wt % to about 10 wt % of isobutylene, about 75 wt % to about 90 wt % of methyl tertiary butyl ether and from about 5 wt % to about 15 wt % of methanol.

The flow of methanol and tertiary butyl alcohol feedstock is regulated so that a molar excess of methanol is present in both the first and second etherification reaction zones, for example, a molar ratio of about 1.1 moles to about 3 moles of methanol per mole of tertiary butyl alcohol. The methanol and isobutylene in the second etherification zone are the unreacted product of the first etherification zone. It is preferred to provide a molar ratio in the first etherification zone of about 2 to 3 moles of methanol per mole of isobutylene. This will provide a molar excess of about 1.1 to 2 moles of methanol per mole of isobutylene to the second etherification reaction zone without excessive reclaiming of methanol.

Contact time is such that about 1 to about 20 volumes of feed mixture per volume of etherification catalyst per hour are fed to the first etherification reaction zone and from about 1 to about 10 volumes of feed mixture per volume of etherification catalyst per hour are fed to the second etherification reaction zone.

Within the first etherification reaction zone, methanol exothermically reacts with tertiary butyl alcohol and in the second etherification zone methanol reacts with isobutylene to form methyl tertiary butyl ether which is contained in a reaction product discharged from the etherification reaction zone to a methyl tertiary butyl ether (MTBE) distillation zone.

As a specific example, when the solid etherification catalyst is a sulfonic acid resin such as Amberlyst® 15 and when the molar ratio of methanol to tertiary butyl alcohol in the feed mixture charged to the first etherification reaction zone is within the ratio of about 2.0 moles of methanol per mole of tertiary butyl alcohol, and the reaction is conducted at a temperature of about 110° C. at a liquid hourly space velocity of about 2.0 volumes of feed mixture per volume of catalyst per hour, the first etherification reaction product may have the composition in part shown by the following table:

| Component | Wt % |
|---|---|
| Water | 14.0 |
| Methanol | 27.6 |
| Isobutylene | 3.0 |
| tBA | 14.1 |
| MTBE | 34.5 |
| Other | 6.8 |

The first etherification reaction product charged to the first MTBE distillation zone is fractionated therein under distillation conditions including a liquid reflux temperature of about 30° C. to about 100° C., and more preferably about 40° C. to about 80° C., a reboiler temperature of about 80° C. to about 115° C., and more preferably from about 95° C. to about 105° C., and a pressure of about 15 psia to about 60 psia, the distillation condition being selected such that substantially all of the MTBE in the etherification reaction product is taken overhead from the first distillation zone. As a consequence, the first distillation fraction taken overhead from the distillation zone will comprise substantially all of the isobutylene and substantially all of the methyl tertiary butyl ether and some of the methanol charged to the first distillation zone. The second heavier distillation fraction discharged from the first MTBE distillation zone will comprise methanol, tertiary butyl alcohol and water.

In accordance with the invention, the first lighter distillation fraction is passed to a second etherification reaction zone. Etherification reaction conditions in the second etherification zone include temperature of about 35° C. to about 130° C., and more preferably from about 40° C. to about 80° C., a pressure of about 50 psia to about 500 psia, and more preferably from about 150 psia to about 250 psia, and a contact time of about 1 to about 10 volumes of first distillation fraction per volume of solid resin etherification catalyst per hour. As a consequence, a portion of the methanol and isobutylene contained in the first distillation fraction will be converted to methyl tertiary butyl ether. Typically, the conversion will amount to about 30 mole % to about 60 mole %, based on the isobutylene.

A second reaction product mixture is formed. The composition of a typical second reaction product mixture is characterized as follows:

| Component | Wt % |
|---|---|
| MTBE | 86.0 |
| Methanol | 7.8 |
| tBA | 1.1 |
| Isobutylene | 2.5 |
| Water | 0.1 |

The second reaction product mixture is typically subjected to solvent extraction to remove methanol and tertiary butyl alcohol.

Within the methanol solvent extraction zone, solvent extraction conditions are established for countercurrent solvent extraction including a ratio of water to extraction feed mixture within the range of about 0.1 to about 0.3 parts of water per part of extraction feed mixture per hour, and more preferably a ratio of about 0.1 to about 0.2 parts of water per part of extraction feed mixture. Extractive conditions to be established may suitably include a temperature of about 20° C. to about 60° C. and more preferably from about 30° C. to about 40° C., and a pressure of about 50 psia to about 500 psia, and more preferably from about 50 psia to about 150 psia.

As a result, a raffinate is formed comprising isobutylene, methyl tertiary butyl ether and a minor amount of water. An extract is formed comprising methanol, water and a minor amount of methyl tertiary butyl ether.

In a preferred embodiment, the raffinate is passed to a second MTBE distillation zone to produce a third lighter distillation fraction comprising isobutylene and water and a fourth heavier distillation fraction consisting essentially of methyl tertiary butyl ether.

This invention is shown by way of Example.

EXAMPLE

Amberlyst® 15 acid resin catalyst was soaked in methanol for 2 days. A 25 cc portion of the presoaked catalyst was charged to a first upflow, tubular reactor.

Another 25 cc portion of the presoaked catalyst was charged to a second upflow tubular reactor.

Feedstock comprising methanol and tertiary butyl alcohol was charged to the first reactor in a molar ratio of 2 to 3 moles of methanol per mole of tertiary butyl alcohol. The first reactor product was fractionated to recover essentially all methyl tertiary butyl ether overhead and passed to the second reactor. Reactor pressure was 214.7 psia.

The following data was recorded:

| Feed Composition To Second Rx | | | | |
|---|---|---|---|---|
| | Ex. 1 wt % | Ex. 2 wt. % | Ex. 3 wt % | Ex. 4 wt % |
| water | 1.0 | 0.3 | 0.1 | 0.1 |
| methanol | 14.5 | 14.7 | 14.9 | 13.1 |
| t-butyl alcohol | 0.74 | 0.78 | 0.84 | 0.86 |
| isobutylene | 9.2 | 8.6 | 8.6 | 12.4 |
| ditertiary butyl peroxide | 0.25 | 0.25 | 0.25 | 0.0 |
| methyl tertiary butyl ether | 73.0 | 75.0 | 75.0 | 73.4 |

| Second Rx - Isobutylene Conversion | | | | |
|---|---|---|---|---|
| | Isobutylone Conversion @ Rx2 Temperature | | | |
| LHSV** | 49° C. | 60° C. | 71° C. | 82° C. |
| | EXAMPLE 1* | | | |
| 2 | 80.4 wt % | — | 71.4 wt % | 60.5 wt % |
| 5 | 51.6 | — | 69.6 | 61.0 |
| 10 | 22.7 | — | 63.3 | 58.6 |

*Water in feed 0.96 wt %; Isobutylene selectivity to MTBE 70-75%
**LHSV - volume feed per volume catalyst per hour

| | EXAMPLE 2* | | | |
|---|---|---|---|---|
| 2 | 81.6 wt % | — | — | 62.7 wt % |
| 5 | 59.1 | — | — | 62.4 |
| 10 | 33.1 | — | — | 61.0 |

*Water in feed 0.30 wt %; Isobutylene selectivity to MTBE 92-94%

| | EXAMPLE 3* | | | |
|---|---|---|---|---|
| 2 | 80.8 wt % | — | — | — |
| 5 | 57.7 | — | — | — |
| 10 | 32.0 | — | — | — |

*Water in feed 0.10 wt %; Isobutylene selectivity to MTBE 94-98%

| | EXAMPLE 4* | | | |
|---|---|---|---|---|
| 2 | 78.1 wt % | 81.9 wt % | 74.8 wt % | 63.9 wt % |
| 5 | 56.1 | 79.2 | 75.3 | 64.6 |
| 10 | 24.3 | 64.7 | 69.0 | 65.0 |

*Water in feed 0.10 wt %, Isobutylene selectivity to MTBE 94-96%

While particular embodiments of the invention have been described, it will be understood, of course, that the invention is not limited thereto since many modifications may be made, and it is, therefore, contemplated to cover by the appended claims any such modification as fall within the true spirit and scope of the invention.

What is claimed is:

1. A continuous process for reacting tertiary butyl alcohol with methanol to produce methyl tertiary butyl ether comprising the steps of:
   a) passing a feed mixture comprising methanol and tertiary butyl alcohol in a molar ratio of 2 to 3 moles of methanol per mole of tertiary butyl alcohol through a first etherification reaction zone containing etherification catalyst under etherification conditions at a liquid hourly space velocity of 1 to 10 volumes feed mixture per catalyst volume per hour to form a first reaction product mixture comprising unreacted methanol, unreacted tertiary butyl alcohol, water, isobutylene and methyl tertiary butyl ether;
   b) passing the first reaction product mixture to a first distillation zone and separating into a first lighter distillate fraction comprising isobutylene, methanol and methyl tertiary butyl ether and a second heavier distillate fraction comprising methanol, tertiary butyl alcohol and water,
   c) passing the first lighter distillate fraction to a second etherification reaction zone containing etherification catalyst under etherification conditions at a liquid hourly space velocity of about 1 to 10 volumes feed mixture per catalyst volume per hour to form a second reaction product mixture comprising unreacted methanol, unreacted isobutylene and methyl tertiary butyl ether,
   d) separating the second reaction product mixture in a solvent extraction zone to produce a raffinate comprising isobutylene and methyl tertiary butyl ether and an extract comprising unreacted methanol, tertiary butyl alcohol and water.

2. The process of claim 1 additionally comprising: passing the raffinate to a second distillation zone and separating it therein into a third lighter distillation fraction comprising isobutylene and water and a fourth heavier distillation fraction consisting essentially of methyl tertiary butyl ether.

3. The process of claim 1 wherein the second heavier distillation fraction comprises less than 1 wt % methyl tertiary butyl ether.

4. The process of claim 1 wherein step (d) the separating is carried out by solvent extraction with water.

* * * * *